(12) United States Patent
Buchanan et al.

(10) Patent No.: US 6,620,958 B2
(45) Date of Patent: Sep. 16, 2003

(54) USE OF MEMBRANES TO SEPARATE ORGANIC LIQUIDS HAVING DIFFERENT POLARITIES

(75) Inventors: J. Scott Buchanan, Lawrenceville, NJ (US); Lawrence J. Altman, Sarasota, FL (US); John W. Diehl, Paulsboro, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 1 day.

(21) Appl. No.: 09/891,908

(22) Filed: Jun. 26, 2001

(65) Prior Publication Data

US 2003/0028044 A1 Feb. 6, 2003

(51) Int. Cl.$^7$ ................................................ C07C 69/96
(52) U.S. Cl. ....................................................... 558/277
(58) Field of Search ......................................... 558/277

(56) References Cited

U.S. PATENT DOCUMENTS

| | | | |
|---|---|---|---|
| 4,798,674 A | 1/1989 | Pasternak et al. | 210/640 |
| 5,498,743 A | 3/1996 | Shih et al. | 558/277 |
| 5,504,239 A | * 4/1996 | Mehl et al. | 558/277 |

* cited by examiner

*Primary Examiner*—Joseph K. McKane
*Assistant Examiner*—Andrea D. Small

(57) ABSTRACT

A method for separating at least one lower polarity fluid from a mixture of fluids having varying polarity, comprising contacting at least one low polarity or non-polar polymeric membrane with the mixture of fluids under conditions such that the at least one lower polarity fluid selectively permeates through the membrane, wherein the membrane is one which has a ratio of heteroatoms chemically bonded to the carbon atoms in the membrane to the number of carbon atoms of less than about 0.2, preferably less than about 0.05.

7 Claims, No Drawings

USE OF MEMBRANES TO SEPARATE ORGANIC LIQUIDS HAVING DIFFERENT POLARITIES

The present invention relates to the separation of organic liquids. More specifically it relates to a process for separating organic liquids based upon their polarity utilizing a low polarity or non-polar membrane.

BACKGROUND OF THE INVENTION

It is well known to separate mixtures of liquids by various techniques including adsorption or distillation. These conventional processes, however, generally have high capital costs. For example, separating liquids by distillation requires expensive distillation towers, heaters, heat exchangers, as well as a substantial amount of auxiliary equipment, such as, pumps, collection vessels, vacuum generating equipment, etc. Distillation operations also generally have high operating costs associated with heating, cooling and material transfer.

Additionally, the specific properties of the materials being separated may warrant equipment or processing beyond that required for simple distillation to complete the separation. For example, when the mixture to be separated forms an azeotrope, the separation may require a series of steps (e.g., use of two or more towers) or by the addition of other materials to the separation system.

Adsorption systems also encounter comparable problems to those associated with distillation.

Thus, it would be advantageous to be able to separate mixtures of materials which are difficult or expensive to separate by distillation or adsorption systems.

The use of membrane technology to separate mixtures which are difficult to separate by distillation or adsorption are known in the art and include the use of porous and non-porous membranes. Non-porous membranes are used to separate mixtures of miscible liquids by exploiting the differences in the rate of transport through the membrane by means of a solution and diffusion mechanism. Methods have been proposed which utilize membranes to separate mixtures of organic substances or water/organic substance mixtures through pervaporation, vapor permeation or perstraction. Although each of these techniques rely upon a solution and diffusion mechanism for transport through the membrane, the operating parameters are quite different.

In the case of pervaporation, the liquid to be subjected to separation is fed on one side of a membrane, while the pressure is decreased or a carrier gas is passed on the other side of the membrane to permeate the material to be separated in the form of a gas through the membrane. Vapor permeation differs in that a vapor of a mixture is fed on the one side of the membrane and the material permeated through the membrane is recovered by cooling and condensing the permeated vapor. Perstraction differs from pervaporation in that the material to be separated is permeated through the membrane as a liquid and the carrier stream is also a liquid.

Examples of methods employing such membrane separations include separation of organic substance/water mixtures using a polymeric membrane having active anionic groups, separation of ethanol/water mixtures using a cellulose acetate membrane or a polyvinyl alcohol membrane, separation of organic substance/water mixtures or organic substance mixtures using a poly acrylonitrile copolymer membrane and separation of organic substance mixtures using a cross-linked polyvinyl alcohol membrane.

U.S. Pat. No. 4,798,674 to Pasternak et al. describes a method for concentrating a charge solution containing a $C_1$–$C_3$ alcohol and an organic oxygenate selected from organic ethers, aldehydes, ketones and esters through pervaporation using a membrane of cross-linked polyvinyl alcohol and a high molecular weight ion exchange resin in membrane form. The alcohol permeates the membrane at a higher rate than the oxygenate, thus concentrating the oxygenate.

The present inventors have unexpectedly discovered that a liquid of reduced polarity relative to a mixture of liquids having varying polarity can be selectively separated from the mixture using a low polarity or non-polar, non-porous membrane.

SUMMARY OF THE INVENTION

The present invention is a method for separating at least one lower polarity fluid from a mixture of fluids having varying polarity.

A method for separating at least one lower polarity fluid from a mixture of fluids having varying polarity, comprising contacting at least one low polarity or non-polar polymeric membrane with the mixture comprising fluids of varying polarity under conditions such that at least one lower polarity fluid selectively permeates through the membrane, wherein the membrane is one which has a ratio of heteroatoms chemically bonded to the carbon atoms in the membrane to the number of carbon atoms of less than about 0.2, preferably less than about 0.05. Preferably, the method includes the step of eluting the at least one lower polarity fluid which has permeated through the membrane. The eluting step includes passing a solvent fluid over the side of the membrane opposite to the side which is contacted with the mixture under conditions such that the lower polarity fluid is carried away from the membrane. The mixture typically comprises fluids of varying polarity, e.g., dimethyl carbonate, ethylene glycol, and methanol, and wherein the lower polarity fluid comprises dimethyl carbonate. It is also desirable to use the method of the present invention when hydrogen is the lower polarity fluid.

The present invention also includes the use of such a membrane integral to a chemical reactor, wherein the mixture comprising the fluid of varying polarity is formed via the reaction of ethylene carbonate and methanol.

Optionally, two or more low polarity or non-polar polymeric membranes are contacted by the mixture in series, wherein the permeated liquid from one membrane contacts the next adjacent membrane and so forth. The membranes preferably have different flux rates and different selectivities relative to the selectively permeable fluid or fluids which contact each respective membrane. The membrane may further comprise a porous support layer and typically is a composite membrane comprising a plurality of polymeric layers.

The present invention also includes a process for producing a dialkyl carbonate which comprises the following steps: (a) reacting an alkanol with an alkylene carbonate, thereby forming a product mixture comprising the dialkyl carbonate, the alkanol, the alkylene carbonate and, optionally, an alkylene glycol; and (b) separating at least a portion of the dialkyl carbonate from the product mixture by contacting at least one low polarity or non-polar polymeric membrane with the product mixture under conditions which produce a permeate comprising the dialkyl carbonate, preferably dimethyl carbonate.

Additional objects, advantages and novel features of the invention will be set forth in part in the description and examples which follow, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE PREFERRED EMBODIMENTS

As used herein and in the claims, the term "lower polarity" when referring to a fluid (e.g., liquid and/or gas) means that the fluid with lower polarity is of relatively lower polarity as compared to at least one other fluid of higher polarity in a mixture of fluids. For example, assume a fluid mixture contained fluid 1, fluid 2, fluid 3, and fluid 4 and that each successively listed fluid was of higher polarity than the preceding listed fluids (i.e., as to polarity: fluid 1<fluid 2<fluid 3<fluid 4). Then each of fluids 1 through 3 could qualify as a fluid of lower polarity, because at least one fluid 4 in the mixture of four fluids is of a higher polarity than each of fluids 1 through 3.

The present invention is a method for separating a mixture of organic fluids (e.g., liquids and/or gases) based upon their relative polarity. More specifically, it is a method for selectively separating a liquid or liquids of relatively lower polarity from a mixture of liquids having varying polarity using a low polarity or non-polar, non-porous polymeric membrane.

The process of the present invention is accordingly suitable, for example, for the following separation tasks, i.e., the removal of dialkyl carbonates from alcohols, the removal of dialkyl carbonates from diols, the removal of dialkyl carbonates from alcohol/water mixtures or diol/water mixtures, the removal of alkyl pyridines from pyridine, and the removal of esters from reaction mixtures containing acids and alcohols as starting materials. The process of the present invention may also be applicable for separating hydrogen from gaseous mixtures, for example, from syngas containing hydrogen, carbon monoxide, carbon dioxide and methane.

Membranes that are useful according to the present invention include those membranes made from polymeric materials which have low polarity or non-polar. The membranes are preferably non-porous polymeric membranes (i.e., non-porous in the sense of not permitting macroscopic sized particles to pass therethrough). The polymeric membranes may be synthetic membranes or they may be made from naturally occurring polymeric materials, for example, naturally occurring latex.

The suitability of a given low polarity or non-polar membrane for use in the present invention may be determined by a competitive diffusion test, in which a mixture of a polar species and a non-polar species is allowed to diffuse through the membrane. One such test is described below in Example 1. A relative diffusivity (i.e., diffusivity of non-polar species divided by diffusivity of polar species) greater than 1 is required, and greater than 3 is preferred.

A membrane useful in the present invention is a low polarity or non-polar latex-based membrane formed from natural latex found in the Hevea brasilensis tree. Natural Hevea latex has been described as a cytoplasmic system containing rubber and nonrubber particles dispersed in an aqueous serum phase. Generally, Hevea natural rubber contains about 93 to 95 wt % Cis-1-4-polyisoprene. The non-rubber portion consists of moisture (0.30–1.0 wt %), acetone extract (1.5–4.5 wt %), protein (20.–3.0 wt %) and ash (0.2–0.5 wt %).

The double bonds in such natural rubber undergo the usual chemical reactions, such as, addition, substitution and epoxidation. Thus, the natural rubber can be treated or modified to change its physical properties. For example, natural rubber can be chlorinated to improve its resistance to chemical attack, reacted with peracids to provide an epoxidized natural rubber which has increased oil resistance and decreased air permeation, or vulcanized (or crosslinked) to improve toughness over a greater range of temperature. The membrane can also be a synthetic low polarity or non-polar latex membrane.

The membrane can also be a synthetic low polarity or non-polar polymeric based membrane, for example, polyisoprene, styrene-butadiene copolymer, or neoprene. The synthetic low polarity or non-polar polymeric membrane may also be composed of a mixture of two or more polymers. The molecular structure of the polymeric membrane will determine its relative polarity. Generally, most unsubstituted aliphatic hydrocarbon or silicone polymers and/or elastomers will have a relatively low polarity or non-polar and will be suitable for use in the present invention, provided that they otherwise exhibit the required physical characteristics.

For carbon-based non-polar polymer membranes, it is preferred that the ratio of heteroatoms, such as oxygen, nitrogen or chlorine, chemically bonded to the carbon atoms in the membrane polymer to the number of carbon atoms be less than 0.2 heteroatoms per carbon atom, and more preferably less than 0.05. Thus, some common condensation polymers, such as nylon 6,6 (polyamide) and polyethylene terephthalate fall outside this preferred range of heteroatom content.

The membranes according to the current invention may also be composed of two or more polymeric layers to form a composite membrane. Preferable, the composite membrane will have a first outer side composed of a low polarity or non-polar polymeric material to provide for the less polar fluid(s) to be separated from the mixture within the first outer side of the membrane. Preferably, the composite membrane will have an inner layer or layers between the first outer side and second outer side of the composite membrane. The inner layers should be of a suitable material to allow diffusion of at least one of the non polar fluids to be separated from the starting mixture of fluids. Optionally, the inner layer may be chosen such that it will allow for diffusion of less than all of the non polar fluids that diffuse into the first outer side of the membrane. For example, the inner layer or layers may be of sufficient number and/or thickness to allow for preferential diffusion of a molecule of smaller diameter from a mixture of fluids with equal polarity. The inner layer or layers are preferably made of a polymeric material. The second outer layer should be chosen to allow for diffusion of the low polarity or non-polar fluid(s) out of the membrane into a second fluid or mixture of fluids. The second outer layer is preferably made of polymeric material.

The physical characteristics required for a given membrane will depend upon the chemical composition, temperature and pressure of both the permeate and raffinate phases in contact with the membrane. Essentially the membrane must maintain its integrity while providing the required separation performance for the substance being separated.

The separation performance for a membrane in accordance with the invention is governed by solution-diffusion processes. Typically, a first fluid mixture (e.g., a gaseous and/or liquid mixture) of materials having varying polarity is contacted with a first face of a suitable low polarity or non-polar membrane and a second solvent fluid is contacted with the second face of the membrane. The membrane is characterized by permitting: (a) sorption in the first face of at least one component of the fluid mixture, e.g., the least polar material in the mixture; (b) diffusion of the one component across the thickness of the membrane; and (c) desorption of the one component from the second face into the solvent fluid. A chemical potential gradient or concentration gradient for the one component is then established across the membrane, the potential or concentration in the first fluid mixture being greater than in the second solvent fluid side.

The overall rate of migration of the one component from the first fluid mixture to the second fluid is dependent upon, inter alia, the following: (1) extent and rate of sorption of that one component in the first face of the membrane; (2) rate of diffusion of the one component through the membrane; and (3) extent and rate of desorption of the one component out of the second face into the solvent fluid.

If either extent or rate of sorption is low then the overall migration rate of the one component will be low regardless of the diffusion rate of the component in the membrane or desorption rate into the solvent fluid. The extent and/or rate of sorption of the one component may be low, for example, because its concentration in the first fluid mixture is low, leading to low rate of transfer of the one component to the first face. Also, the one component may appreciably swell or plasticize the first face and in doing so permit sorption of other components from the first fluid mixture into the first face. Such swelling may be restrained by incorporating crosslinks in the membrane, by blending (i.e., alloying) the material of the membrane with substances (e.g., polymers) which are not swollen by the one component, by adding substances which reduce the affinity of the membrane for the one component, and by inducing the formation of micro crystals in the latex material of the membrane. Further, the characteristic dimensions of the interstices in the surface region of the membrane in the steady-state under operating conditions should generally be of a size which discourages sorption of unwanted components.

Generally the rate of diffusion of the one component increases as its diameter decreases. However, among components having substantially the same diameter, those of greater length (i.e., greater aspect ratio) will generally diffuse less rapidly. Components having great lengths (e.g., polymers) may not diffuse at all even though they have small diameters in the extended (e.g., solvated or diffused) form and appreciable sorption (so-called "snake-cage" effect). The interstices in the material of the membrane must be appreciably larger than the characteristic dimension of the diffusing component (e.g., the one component). In some instances the overall permeability can be quite high, even though the extent or sorption is low, owing to exceptionally large diffusion coefficients. In some processes (e.g., pervaporation) the rate of desorption of sorbed components into the solvent fluid in contact with the second face of the membrane can be so high and/or the chemical potential of the desorbed components in the solvent fluid so low that the second face is essentially free of sorbed components. In such a case, the overall rate of migration of the one component may be almost entirely determined by the slow diffusion in the second face. Small molecules and/or molecules having high affinity for the material of the membrane will then be favored.

If either the extent or rate of desorption is low, then the overall migration rate of the one component will be low regardless of the diffusion rate of the component across the membrane or sorption rate from the first fluid mixture into the first face. The extent of desorption may be low because the chemical potential of the one component in the solvent liquid is not sufficiently low compared to the chemical potential in the second face of the membrane. This may, for example, be due to lack of sufficient diffusion and convection to remove the desorbed one component from the vicinity of the second face. On the other hand, the chemical potential of the one component in the second solvent fluid may be so low that there is essentially no sorbed component (s) in the second face resulting in very low diffusion rates in the face.

The overall rate of migration and selectivity will be affected by the specific composition of the membrane and the physical characteristics (e.g., polarity) of the polymer employed. For example, the proportions of elastomer, fillers, softeners and vulcanizing agents present in the compounded latex rubber can affect the selectivity and rate of migration. The molecular weight and viscosity of the polymer or elastomer, and the thickness of the membrane, can also affect the rate of migration.

Preferably, the addition of fillers and softeners will be avoided or minimized, so that the membrane will contain none or only small amounts of such additives or impurities, because of the negative influence on the permeability of the membrane. The membrane will generally be vulcanized (or cross-linked) by heating during the preparation process of the membrane or, optionally, by the addition of a small amount of a vulcanizing or cross-linking agent during the preparation process.

The low polarity or non-polar latex membrane of the current invention can be prepared in the form of a film by any process known in the art, such as, for example, casting or coating an aqueous dispersion or emulsion followed by drying. Such an aqueous dispersion will generally contain about 5 to 10 wt % elastomer, e.g., polyisoprene, and a crosslinking or vulcanizing agent, e.g., sulfur or sulfur species.

A membrane useful in the present invention will preferably include a non-porous layer of a suitable low polarity or non-polar polymer having a thickness of about 0.1 to 15 mils, preferably 0.5 to 5 mils. Preferably, the non-porous layer will be incorporated into a composite structure which contains a carrier layer, having a high degree of porosity and mechanical strength. The carrier layer can comprise a layer of any suitable material, such as, a fibrous or non-fibrous, woven or non-woven cloth or mesh, a wire or metal mesh, or glass fibers. The carrier layer can be any porous, flexible, material which is compatible with the chemical system being contacted and which provides sufficient mechanical properties under the specific operating conditions.

The membrane can be of any configuration which prevents the flow of liquid from one side of the membrane to the other by any means other than through the membrane itself. Typical configurations include any configuration known in the art, such as, flat sheets or films, tubes or hollow fibers. Although the use of a single membrane is typical, the use of a series of membranes having different rates of permeation and selectivity is also contemplated. Generally, when such a series of membranes are employed, the mixture of liquids having varying polarity will be contacted successively with the membranes so that the permeated liquid from one membrane is contacted with the next membrane in succession. Typically, the membranes will be arranged so that they are contacted in order of decreasing rate of permeation and increasing selectivity.

The process of the present invention is particularly useful for separating organic liquids having varying polarities that are difficult or costly to separate by other methods, such as, distillation. For example, mixtures of liquids, such as, dimethyl carbonate and methanol, are difficult to separate by distillation because an azeotrope is formed. However, since dimethyl carbonate is less polar than methanol and will selectively permeate through the low polarity or non-polar membranes of the present invention at a faster rate than the methanol, it can be selectively separated from the mixture.

The present process can be carried out under pervaporation conditions, in which the mixture of fluids (e.g., liquids or gases) having varying polarity is contacted with one side of the low polarity or non-polar, non-porous membrane. The less polar fluid to be separated from the mixture absorbs into the membrane and diffuses therethrough, as discussed above. The permeate side of the membrane is maintained at a pressure which is lower than the vapor pressure of the permeate. Preferably, the permeate side of the membrane is maintained at a low pressure below about 10 mm Hg. The permeate which passes through the membrane and exits as a vapor may be recovered by condensing at low temperature or alternatively may be swept away by use of a moving stream of gas. Examples of separations under pervaporation conditions that are contemplated include separating methane from a mixture of methane and water vapor, and CO (or possibly $CO_2$) from syngas.

The present process can also be carried out under perstraction conditions, in which the mixture of liquids having varying polarity is contacted with one side of the low polarity or non-polar, non-porous membrane. The less polar liquid to be separated from the mixture absorbs into the membrane and diffuses therethrough. The permeate which passes through the membrane is swept away with a liquid solvent stream. The solvent can generally include any substance in which the permeated substance being separated will dissolve into or readily mix with. Preferably, a solvent will be chosen which can easily be separated from the desired permeated liquid. Typical solvents can include, for example, methanol, heptane, pentane, hexane, cyclohexane, or any other non-reactive, low boiling organic solvent.

The process conditions of the present invention will vary depending on the composition of the mixture to be separated and the required performance criteria of the specific membrane, since the temperature can effect the diffusion rate through the membrane and, thus, may effect the overall rate and selectivity. For example, dimethyl carbonate produced by the transesterification reaction of ethylene carbonate with methanol can be separated from the reactor effluent stream by a process according to the present invention by contacting the mixture (e.g., reaction effluent) on a first side of the membrane at temperatures up to about 260° C. Although the pressure is not critical, since the rate of permeation is controlled by a solution/diffusion mechanism, contacting mixtures having pressures up to about 5000 psia are contemplated, with pressure differentials across the membrane up to 600 psi being contemplated. The permeate side of the membrane will preferably be maintained under a vacuum when operating under pervaporation conditions.

The process of the present invention may find particular use when the mixture of liquids having varying polarity is an effluent stream from a reactor wherein one of the components to be separated is a product of the reaction. An example of such an effluent stream is that obtained from the reaction of methanol and ethylene carbonate, wherein the effluent stream may contain unreacted methanol, unreacted ethylene carbonate, product dimethyl carbonate and product ethylene glycol, and wherein the product to be separated is dimethyl carbonate.

It is contemplated that the effluent stream from such a reactor may have been subjected to preliminary separation, e.g., distillation, to yield, for example, an azeotrope of methanol and dimethyl carbonate.

Thus, in one embodiment, the process of the present invention will be incorporated into the purification steps of a chemical synthesis, e.g., dialkyl carbonate production.

In another embodiment, the process of the present invention can be incorporated into the reactor itself. This will be particularly useful in connection with an equilibrium reaction wherein a reaction product is selectively withdrawn from the reaction mixture. By withdrawing the reaction product, the equilibrium can be shifted to increase yield and selectivity and possibly reduce the amount of reactants or recycle to the reactor. An example of such a reaction is the transesterification reaction between an alkanol and an alkylene carbonate which produces dialkyl carbonate and alkylene glycol.

The reactants to the transesterification reaction (e.g., ethylene carbonate and methanol) are typically contacted in the presence of a transesterification catalyst. The transesterification catalyst can typically include any homogeneous or heterogeneous catalyst known in the art which provides adequate reaction kinetics.

Examples of such catalysts include: alkali metals or alkaline earth metals, such as, lithium, sodium, potassium, rubidium, cesium, magnesium, calcium, strontium, barium and the like; basic compounds such as hydrides, hydroxides, alkoxides, aryloxides and amides of alkali metals or alkaline earth metals and the like; basic compounds, such as, carbonates and hydrogencarbonates of alkali metals or alkaline earth metal, alkali metal or alkaline earth metal salts of organic acids and the like; tertiary amines, such as, triethylamine, tributylamine, trihexylamine, benzyldiethylamine and the like; nitrogen-containing heteroaromatic compounds, such as, N-alkylpyrrole, N-alkylindole, oxazole, N-alkylimidazole, N-alkylpyrazole, oxadiazole, pyridine, alkylpyridine, quinoline, alkylquinoline, isoquinoline, alkylisoquinoline, acridine, alkylacridine, phenanthroline, alkylphenanthroline, pyrimidine, alkylpyrimidine, triazine, alkyltriazine and the like; cyclic amidines, such as, diazabicycloundecene (DBU), diazabicyclononene (DBN) and the like; thallium compounds, such as thallium oxide, thallium halides, thallium hydroxide, thallium carbonate, thallium nitrate, thallium sulfate, thallium salts of organic acids and the like; tin compounds, such as, tributylmethoxytin, tributylethoxytin, dibutyldimethoxytin, diethyldiethoxytin, dibutyldiethoxytin, dibutyldiphenoxytin, diphenyldimethoxytin, dibutyltin acetate, tributyltin chloride, tin 2-ethylhexanoate and the like; zinc compounds, such as, dimethoxyzinc, diethoxyzinc, ethylenedioxyzinc, dibutoxyzinc and the like; aluminum compounds, such as, aluminum trimethoxide, aluminum triisopropoxide, aluminum tributoxide and the like; titanium compounds, such as, tetramethoxytitanium, tetraethoxytitanium, tetrabutoxytitanium, dichlorodimethoxytitanium, tetraisopropoxytitanium, titanium acetate, titanium acetylacetonate and the like; phosphorus compounds, such as, trimethylphosphine, triethylphosphine, tributylphosphine, triphenylphosphine, tributylmethylphosphonium halides, trioctylbutylphosphonium halides, triphenylmethylphosphonium halides and the like; zirconium compounds, such as, zirconium halides, zirconocenes, zirconium acetylacetonate, zirconium alkoxides, zirconium acetate and the like; lead and lead-containing compounds, such as, lead oxides, e.g., PbO, $PbO_2$, $Pb_3O_4$ and the like; lead sulfides, such as, PbS, $Pb_2S_3$, $PbS_2$ and the like; lead hydroxides, such as, $Pb(OH)_2$, $Pb_3O_2(OH)_2$, $Pb_2[PbO_2(OH)_2]$, $Pb_2O(OH)_2$ and the like; plumbites, such as, $Na_2PbO_2$, $K_2PbO_2$, $NaHPbO_2$, $KHPbO_2$ and the like; plumbates, such as, $Na_2PbO_3$, $Na_2H_2PbO_4$, $K_2PbO_3$, $K_2[Pb(OH)_6]$, $K_4PbO_4$, $Ca_2PbO_4$, $CaPbO_3$ and the like; lead carbonates and basic salts thereof, such as, $PbCO_3$, $PbCO_3.Pb(OH)_2$ and the like; alkoxylead compounds and aryloxylead compounds, such as $Pb(OCH_3)_2$, $(CH_3O)Pb(OPh)$, $Pb(OPh)_2$ and the like; lead salts of organic acids, and carbonates and basic salts thereof, such as, $Pb(OCOCH_3)_2$, $Pb(OCOCH_3)_4$, $Pb(OCOCH_3)_2.PbO.3H_2O$, and the like; organolead compounds, such as, $Bu_4Pb$, $Ph_4Pb$, $Bu_3PbCl$, $Ph_3PbBr$, $Ph_3Pb$ (or $Ph_6Pb_2$), $Bu_3PbOH$, $Ph_2PbO$ and the like wherein Bu represents a butyl group and Ph represents a phenyl group; lead alloys, such as, Pb—Na, Pb—Ca, Pb—Ba, Pb—Sn, Pb—Sb and the like; lead minerals, such as galena, zinc blende and the like; hydrates of these lead compounds; ion-exchangers, such as, anion-exchange resins having teriary amino groups, amide groups, or at least one type of ion-exchange group selected from the group consisting of sulfonate, carboxylate and phosphate groups; strongly basic solid anion-exchangers having quarternary ammonium groups as ion-exchange groups and the like; solid inorganic compounds, such as, silica, silica-alumina, silica-magnesia, aluminosilicate, gallium silicate, various types of zeolites, various types of metal-exchanged zeolites, ammonium-exchanged zeolites; and mixtures thereof.

Preferred homogeneous transesterification catalysts include alcoholates and alkali hydroxides and carbonates, such as, sodium methylate and sodium hydroxide. Preferred heterogeneous transesterification catalysts include anion exchange resins having tertiary amine, quaternary ammonium, sulfonic acid or carboxylic acid functional groups, solid support catalysts containing alkaline earth metal halides, such as, those described in U.S. Pat. No. 5,498,743, which is incorporated herein by reference, or inorganic solid support catalysts alone, such as, alumina, pseudoboehmite, MgO and $MgO/Al_2O_3$ hydrotalcites, or containing ions, metals, compound or complexes of at least one element of Groups 1, 2, 4–10, 12 and 13–17 (IUPAC classification, previously Groups 1A, 2A, 4B–8B, 2B and 3A–7A) of the Periodic Table.

The catalyst can be utilized as a solid, as a solubilized solid, or in liquid form with the preferred form being that of a solubilized solid. A solid catalyst, such as, an alkali metal carbonate or alkali metal halide can be solubilized in one or more of the alkylene carbonate stream, alkanol stream or another stream that may be conveyed to the reacted vessel. A solid catalyst may also be employed in a fixed bed or ebullated bed arrangement or may be fluidized in a manner so as to enhance the transesterification reaction.

Transesterification reaction conditions generally comprise a reaction temperature ranging from about 32° F. (0° C.) to about 500° F. (260° C.), preferably from about 70° F. (21° C.) to about 400° F. (204° C.), and more preferably from about 100° F. (38° C.) to about 300° F. (149° C.). Excessively high temperatures can result in the decomposition of the dialkyl carbonate into undesirable thermolysis products, such as, carbon dioxide and possibly reduced yield or selectivity of the membrane. Exceedingly low temperatures can result in reduced alkylene carbonate and alkanol conversion. Suitable reaction pressures generally range from about 0 psig to about 5000 psig, preferably from about 50 psig to about 1000 psig, and more preferably from about 50 psig to about 500 psig. Excessively low pressures can result in vaporization of the alkanol resulting in carryover of the alkanol with the dialkyl carbonate-containing product.

In such a reaction, the latex-based low polarity or non-polar, non-porous membrane, preferably a polyisoprene membrane, will be incorporated into a transesterification reactor used to react ethylene carbonate and methanol to produce dimethyl carbonate and ethylene glycol. By utilizing such a membrane in accordance with the present invention, the dimethyl carbonate product from the reaction zone can be selectively separated and withdrawn from the reaction mixture as permeate.

The raffinate stream will generally contain ethylene glycol, a small amount of dimethyl carbonate, unreacted methanol and unreacted ethylene carbonate. It may also contain homogeneous transesterification catalyst, if used. The raffinate stream containing the unreacted ethylene carbonate can be recycled to the transesterification reactor or possibly directed to a hydrolysis reactor for converting unconverted ethylene carbonate to ethylene glycol.

The membrane separation process can be operated under pervaporation or perstraction conditions. Under pervaporation conditions, the permeate side of the membrane will typically be maintained under a vacuum and a sweep stream of an inert gas, e.g., $N_2$, can be used to sweep the vapor phase permeate stream, which contains the dimethyl carbonate, away from the membrane. Under perstraction conditions, a liquid solvent stream, e.g., heptane, will be employed to sweep the liquid phase permeate stream, which contains the dimethyl carbonate, away from the membrane.

In certain circumstances it may be beneficial to utilize a solvent which will be used with the substance being separated. For example, in the case of a permeate stream containing an alkyl carbonate, which will be used as an oxygenate additive for gasoline, a suitable gasoline blending component may be employed as the sweep stream solvent, thus avoiding a separation step for the alkyl carbonate and the solvent.

The examples set forth below are for illustration purposes only. The scope of the present invention is not in any way limited by the examples set forth below.

EXAMPLES

Static experiments were performed in which various mixtures of organic substances were placed on one side of a low polarity or non-polar latex membrane and a solvent was placed on the other side of the membrane. The static system was maintained at about 70° F. (21° C.) and the composition on each side of the membrane was measured by GC as a function of time.

Example 1

In this example, a mixture containing 3.72 grams of dimethyl carbonate (DMC) and 3.25 grams of ethylene carbonate (EC) was combined with 10 ml of methanol (MeOH). The combination was placed inside a Trojan® brand non-lubricated latex condom, as commercially available from Youngs Rubber Co., division of Carter-Wallace, New York, N.Y. The condom was tied off and suspended in a solvent of 200 ml of MeOH contained in a glass beaker. The composition of the combination inside the condom (side 1) and of the solvent outside of the condom (side 2) was measured by gas chromatography over a period of 24 hours. The results are listed below in Table 1.

TABLE 1

Results of Static Experiment For DMC and EC (in wt %)

| Time (hours) | DMC (side 1) | EC (side 1) | DMC (side 2) | EC (side 2) |
|---|---|---|---|---|
| 0 | 54 | 46 | | |
| .25 | 51 | 49 | 100 | 0 |
| .83 | 52.6 | 47.4 | 100 | 0 |
| 2.25 | 52 | 48 | 96.5 | 3.4 |
| 5.75 | 46.2 | 53.8 | 95 | 5 |
| 24 | 20 | 80 | 88.4 | 11.6 |

A review of Table 1 reveals that DMC diffuses through the latex membrane faster than EC.

Example 2

In a static experiment similar to Example 1, 10 mls of a reaction product from a zeolite catalyzed transterification reaction, containing 9.3 wt % DMC, 50.1 wt % hydroxyethyl methyl carbonate (HMC), 28.4 wt % EC and 12.2 wt % ethylene glycol (EG), was placed inside the Trojan® brand latex condom (side 1) and tied off. The condom was then suspended in 400 mls of MeOH (side 2). The composition of each side was measured by GC over a period of 48 hours. On side 1 the composition was determined for DMC, HMC and EC as wt % of the total mixture. The amount of EG as a function of time was not recorded. On side 2 the composition was determined for DMC, HMC and EC as wt % relative to each other. The results are listed below in Table 2.

TABLE 2

Results of static Experiment For DMC, HMC and EC (in wt %)

| Time (hours) | DMC (side 1) | HMC (side 1) | EC (side 1) | DMC (side 2) | HMC (side 2) | EC (side 2) |
|---|---|---|---|---|---|---|
| 0 | 9.3 | 50.1 | 28.4 | | | |
| 1.3 | | | | 86.5 | 5.4 | 8.1 |
| 3.75 | 7 | 53.8 | 27.1 | 77.6 | 11.1 | 11.3 |
| 21.5 | 2.6 | 55.3 | 29.2 | 68.5 | 13.6 | 17.9 |
| 28 | 1.2 | 57.8 | 28 | 62 | 18 | 20 |
| 48 | | | | 57.9 | 18.1 | 23.8 |

A review of Table 2 reveals that DMC diffuses through the latex membrane faster than HMC. Although the amount of EG was not quantified in the table above, it was noticed that it primarily remained on side 1 of the latex membrane demonstrating that DMC diffuses through the latex membrane faster than EG.

Example 3

In a static experiment similar to Example 1, a mixture of 5.0 grams of DMC and 15 grams of MeOH was placed on side 1 of the latex condom membrane and 200 mls of heptane was placed on side 2 of the latex condom membrane. The composition of each side was measured by GC over a period of 20 hours. The results are listed below in Table 3.

TABLE 3

Results of Static Experiment For DMC and MeOH (in wt %)

| Time (hours) | DMC (side 1) | M (side 1) | DMC (side 2) | M (side 2) |
|---|---|---|---|---|
| 0 | 16.3 | 83.7 | | |
| 1.67 | 6.8 | 93.2 | 30.7 | 69.3 |
| 20 | 6.3 | 93.7 | 24.3 | 75.6 |

A review of Table 3 reveals that DMC diffuses through the latex membrane faster than MeOH.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A process for producing a dialkyl carbonate which comprises the following steps:
    (a) reacting an alkanol with an alkylene carbonate, thereby forming a product mixture comprising said dialkyl carbonate, said alkanol and said alkylene carbonate; and
    (b) separating at least a portion of said dialkyl carbonate from said product mixture by contacting at least one low polarity or non-polar polymeric membrane with said product mixture under conditions which produce a permeate comprising said dialkyl carbonate in a concentration higher than in said product mixture from step (a).

2. The process of claim 1, wherein said product mixture further comprises an alkylene glycol.

3. The process of claim 1, wherein said dialkyl carbonate is dimethyl carbonate.

4. The process of claim 1, wherein said membrane is one which has a ratio of heteroatoms chemically bonded to the carbon atoms in said membrane to the number of carbon atoms of less than about 0.2.

5. The method of claim 4, wherein said ratio is less than about 0.05.

6. A method for separating at least one lower polarity fluid from a mixture of fluids having varying polarity, the method comprising:
    contacting at least one low polarity or non-polar polymeric membrane with said mixture of fluids comprising fluids of varying polarity, at a pressure differential up to 600 psia, such that at least one lower polarity fluid selectively permeates through said membrane.

7. A process for producing a dialkyl carbonate, the process comprising:
    (a) reacting an alkanol with an alkylene carbonate at a temperature up to 260° C. and at a pressure of up to 5000 psia, thereby forming a product mixture comprising said dialkyl carbonate, said alkanol and said alkylene carbonate; and
    (b) separating at least a portion of said dialkyl carbonate from said product mixture by contacting at least one low polarity or non-polar polymeric membrane with said product mixture under conditions which produce a permeate comprising said dialkyl carbonate in a concentration higher than in said product mixture from step (a) at a pressure differential up to 600 psia.

* * * * *